United States Patent [19]

Epler et al.

[11] Patent Number: 5,135,473
[45] Date of Patent: Aug. 4, 1992

[54] ACHILLES TENDON WRAP

[76] Inventors: Marcia Epler, 350 Green Meadow La., Horsham, Pa. 19044; Paul Krajewski, 15 Rutgers Dr., Delran, N.J. 08075

[21] Appl. No.: 648,750

[22] Filed: Jan. 31, 1991

[51] Int. Cl.⁵ .................... A61F 13/00; A61F 15/00; A61L 15/00
[52] U.S. Cl. ........................ 602/62; 602/65; 2/22; 2/24; 606/201
[58] Field of Search ............... 128/157, 165, 166, 169, 128/171, 80 H; 2/22, 24, 44; 606/201, 203

[56] References Cited

U.S. PATENT DOCUMENTS

| | | | |
|---|---|---|---|
| 3,209,517 | 10/1965 | Hyman | 128/165 |
| 3,383,708 | 1/1965 | Pappas. | |
| 3,506,000 | 8/1968 | Baker. | |
| 3,508,544 | 4/1970 | Moore et al. | 128/157 |
| 4,133,311 | 1/1979 | Karczewsji. | |
| 4,409,976 | 10/1983 | Pence. | |
| 4,590,932 | 5/1986 | Wilkerson | 128/166 |
| 4,727,863 | 3/1988 | Nelson. | |
| 4,769,854 | 9/1988 | Williams. | |
| 4,811,727 | 3/1989 | Etienne. | |
| 4,841,957 | 6/1989 | Wooten et al. | |

FOREIGN PATENT DOCUMENTS

| | | | |
|---|---|---|---|
| 0313487 | 4/1989 | European Pat. Off. | 128/166 |
| 2607383 | 6/1988 | France. | |

OTHER PUBLICATIONS

"New Achilles Tendon Strap", Podiatric Products, p. 8, Sep. 1990.

Primary Examiner—Randall L. Green
Assistant Examiner—Paul Prebilic
Attorney, Agent, or Firm—Ferrill, Logan, Johns & Blasko

[57] ABSTRACT

The present invention is an Achilles tendon brace which comprises: a wrap holding a multidimensional compressive pad; an anatomically proportioned strapping system; and hook and loop fasteners such as available under the trademark Velcro. The compressive pad contains a raised portion which lays above and perpendicular to the Achilles tendon, providing a compressive conuterforce, relieving strain and dispersing pressure normally transmitted through the tendon. The pad conforms to each individual's Achilles tendon with continued use, providing a customized unit providing multidimensional support and compression of the tendon. The strapping system employs straps which are proportioned to match the contours of the Achilles tendon area of the leg, permitting full range of motion of the ankle and foot. The strapping system permits the wrap to be placed snugly around the Achilles tendon, and, in conjunction with the hook and loop fasteners (e.g. Velcro), ensures there is no slippage while providing consistent support throughout activity.

14 Claims, 3 Drawing Sheets

ACHILLES TENDON WRAP

BACKGROUND OF THE INVENTION

1. Field of the Invention

The present invention is directed to a device designed to aid in the treatment and healing of the Achilles tendon when strained or otherwise inflamed. Specifically, the invention is directed to a novel wrap which can be worn during any activity, providing constant support throughout without interfering with the range of motion of a patient's ankle or foot, and which provides pain free motion while aiding the tendon's healing process.

2. Description of the Prior Art

Achilles tendinitis is a common affliction affecting a large number of individuals and is especially prevalent among athletes and others who are highly active. Runners seem particularly prone to this form of tendinitis, which is responsible for nearly one-fifth of the foot and ankle problems experienced by runners.

Once the Achilles tendon has become inflamed, an individual experiences soft tissue swelling, tenderness in the tendon area, and crepitus, a roughening about the tendon. Further, Achilles tendinitis causes a loss of comfort and mobility during periods of activity, often resulting in the bringing about of other afflictions, such as posterior heel pain.

Achilles tendinitis is currently treated in a variety of ways, including: rest; the use of anti-inflammatory agents, such as ice and ultrasound treatments; adhesive strappings; heel pads placed in the shoe; and, in extreme cases, surgery. Many athletes take preventative measures, including the use of ankle braces, elastic wraps and tape, in an attempt to avoid injury to the Achilles tendon.

Athletes and workers are often expected to continue engaging in their normal activities despite suffering from the tendinitis. To do so usually requires the use of a combination of the treatments and preventative measures mentioned above in order to avoid continued or further damage to their bodies. Although all of these measures are helpful to some degree, using them in an attempt to progress individuals back to full activity prior to a full recovery tends to result in reoccurrence of pain and inflammation, an inability of the tendon to accept the necessary dynamic load, or both. As an example, although the use of heel pads in shoes aids in reducing the tensile loading stresses placed on the tendon, it creates an adaptive shortening, predisposing the user to further risk of injury.

There are different problems connected with the employment of adhesive taping techniques, used to provide relief and support during activity. These are common problems associated with the use of tape, such as discomfort resulting from the pull of the tape on the skin, the cost of daily use, the pain and nuisance of removing the tape after use, and, most importantly, the loosening of the tape after approximately ten minutes of activity, which renders the support useless.

Recognizing the drawbacks of these treatments, several prior art devices have been introduced in an attempt to provide relief from the pain of tendinitis during recovery, including U.S. Pat. No. 4,841,957 to Wooten et al. and U.S. Pat. No. 4,811,727 to Etienne. Wooten provides a brace for treating posterior heel pain which fits around the foot and ankle. The brace however is bulky, and the cushioning provided to aid in relieving pain will again produce adaptive shortening which may cause further injury. Etienne teaches the use of an elastic retention stocking for the entire lower limb. The device does not guard against slippage, and thereby may fail to maintain consistent support throughout activity. Further, the stocking contains a heel piece, once again raising concerns about adaptive shortening.

It is therefore the primary object of the present invention to provide an Achilles tendon brace in the form of a wrap which provides constant support of the tendon, aiding in the treatment and healing of the tendon and thereby overcoming the limitations and disadvantages of the prior art.

It is also an object of the present invention to provide a brace to be applied to the Achilles tendon area of a patient's leg which provides a compressive counterforce through a perpendicular moment arm, dispersing the force transmitted through the Gastroc Soleus complex through the brace rather than through the tendon, and relieving the stresses of contraction on the Achilles tendon inferior, thereby permitting a decrease in inflammation.

Another object of the invention is to provide a brace which is easy to apply and is reusable.

A further object of the invention is to provide a brace with fastening means, in the form of anatomically proportioned straps, to prevent slippage or loosening and to maintain consistent support of the tendon even during strenuous activity.

Yet another object of the invention is to provide a multidimensional compressive pad which will conform to the tendon and provide multidimensional compression perpendicular to the line of pull of the muscle-tendon unit.

An additional objective of the invention is to provide an Achilles tendon support strap which does not interact with or cross the ankle or foot.

A still further object of the invention is to provide a novel wrap which is lightweight and able to be worn during any activity, which doesn't interfere with the range of motion of a patient's ankle or foot, and which provides pain free motion while aiding the tendon's healing process.

These and other objects of the present invention and the various features and details thereof are hereinafter set forth in the following detailed description of the invention.

SUMMARY OF THE INVENTION

In accordance with the present invention an Achilles tendon brace is disclosed. The invention comprises a wrap holding a multidimensional compressive pad, an anatomically proportioned strapping system, and hook and loop fasteners such as available under the trademark VELCRO. The compressive pad contains a perpendicular moment arm which allows any force directed through the Achilles tendon to be alternatively transmitted through the pad. The compressive pad conforms to the Achilles tendon with continued use, providing multidimensional compression and support of the tendon. The strapping system employs straps which are proportioned to match the contours of the Achilles tendon area of the leg, permitting full range of motion of the ankle and foot. The strapping system permits the wrap to be secured snugly around the Achilles tendon, and, in conjunction with the hook and loop fasteners (e.g. VELCRO), ensures there is no slippage or loosening, and provides consistent support throughout any activity.

DETAILED DESCRIPTION OF THE DRAWINGS

Figure 1:
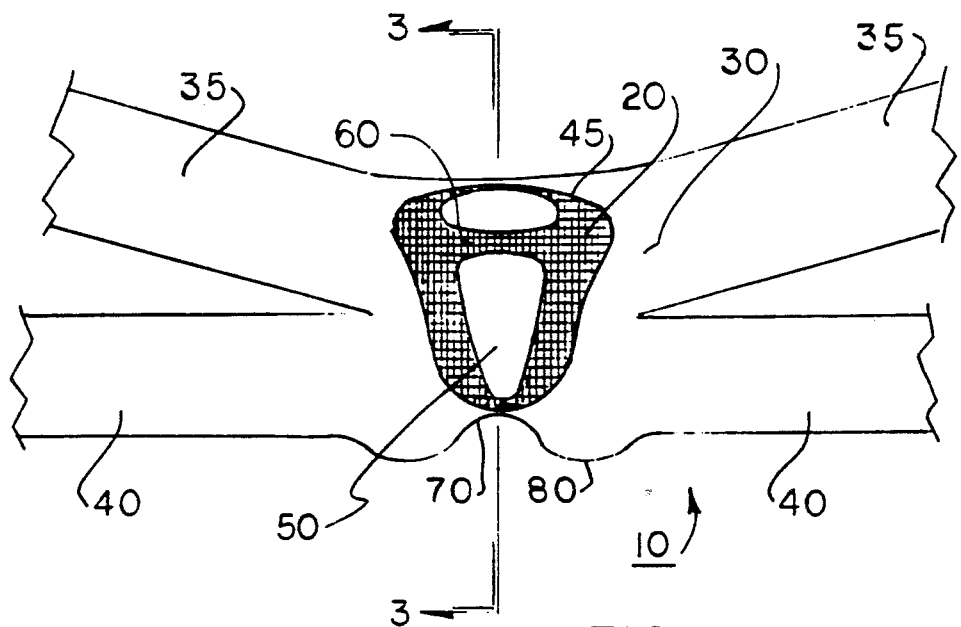
FIG. 1 is a front view of the present invention.
Figure 2:
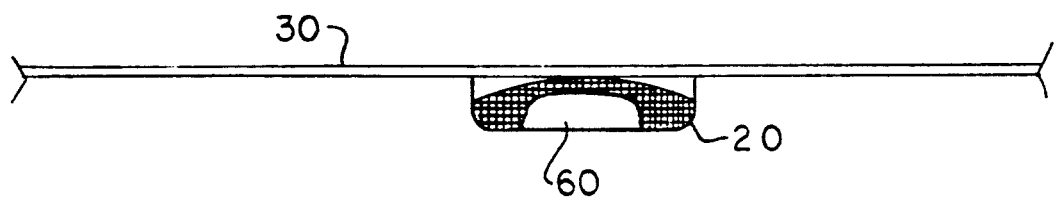
FIG. 2 is a top view of the present invention.

The present invention is described with reference to the enclosed Figures wherein the same numbers are used as applicable. FIGS. 1, 2, 3 and 4 illustrate the present invention prior to its placement on a patient's leg. The wrap 10 consists of a multidimensional pad 20 attached to an anatomically proportioned strap 30. The strap has two superior arms 35 and two inferior arms 40. The inferior arms 40 emerge from both sides of the wrap 10 at a perpendicular to the line of pull of the Achilles tendon. The superior arms 35 emerge at an upward angle of approximately thirty (30) degrees. The difference in angles provides for a better fit when the wrap 10 is secured to a patient's leg, and eliminates slippage of the wrap 10 during prolonged activity.

The pad 20 is substantially triangular in shape, and is secured to the strap 30 in an inverted position. The pad 20 must be made of a material which is durable and dense, yet possess the ability to mold and conform to an individual's lower leg and Achilles tendon. Materials may include neoprene, PLASTAZOTE, and closed cylinders of air or gel. The base 45 of the pad 20 is aligned with superior edge of the strap 30. The remainder of the pad 20 tapers distally. The tapering is in accordance with the normal structural tapering of the distal portion of the leg, and allows the pad to conform to a leg's structure. In the preferred embodiment, the base 45 is essentially flush with the superior edge of the strap 30. The pad 20, in conforming to an individual's lower leg, surrounds the Achilles tendon region and provides multi-dimensional support of the tendon along a majority of the length.

Figure 3:
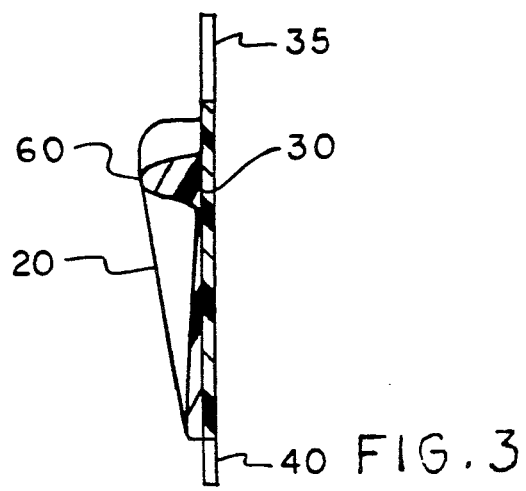
FIG. 3 is a sectional view of the present invention along line 3—3 of FIG. 1.
Figure 4:
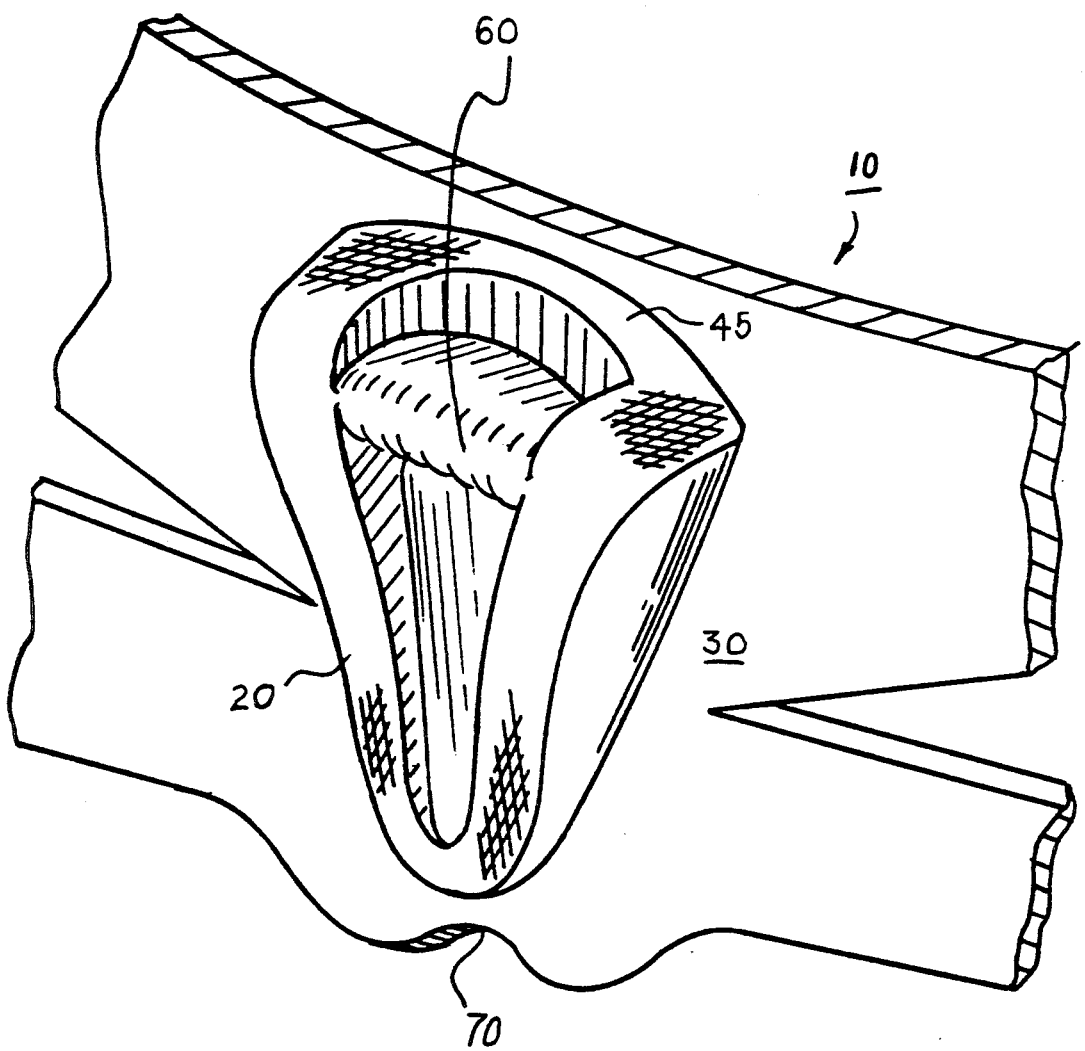
FIG. 4 is a three-quarter isometric view of the present invention.

The anterior surface of the pad has a cut-out channel 50 running proximally to distally in order to accommodate the prominence of the Achilles tendon. As best illustrated in FIG. 3, near the top of the channel 50, a portion of the pad 20 is raised transversely, providing a bump 60 perpendicular to the channel 50. The bump 60 runs in a medial-lateral direction to provide a counterforce perpendicular to the line of pull of the Achilles tendon. The bump 60 provides a moment arm through which stresses and forces normally placed on the Achilles tendon, particularly those transmitted through the Gastroc Soleus complex, are dispersed, relieving the stresses of contraction on the Achilles tendon inferior. In its preferred embodiment, the height, that is to say the anterior-posterior thickness, of the bump 60, is approximately one-half (½) inch, and its superior-inferior width is approximately one-half (½) inch as well. The length of the bump 60 is equivalent to the width of the channel 50 at that point.

The pad 20 may be secured to the strap 30 in any number of ways, such as gluing means or stitching means. The inferior edge 80 of the wrap 10 has a rounded inverted V-shaped notch 70. The notch 70 can be used as an alignment point to align the distal portion of the Achilles tendon with the proper position on the pad 20. The inferior portion of the pad 20 is essentially flush with center of the notch 70.

Figure 5:
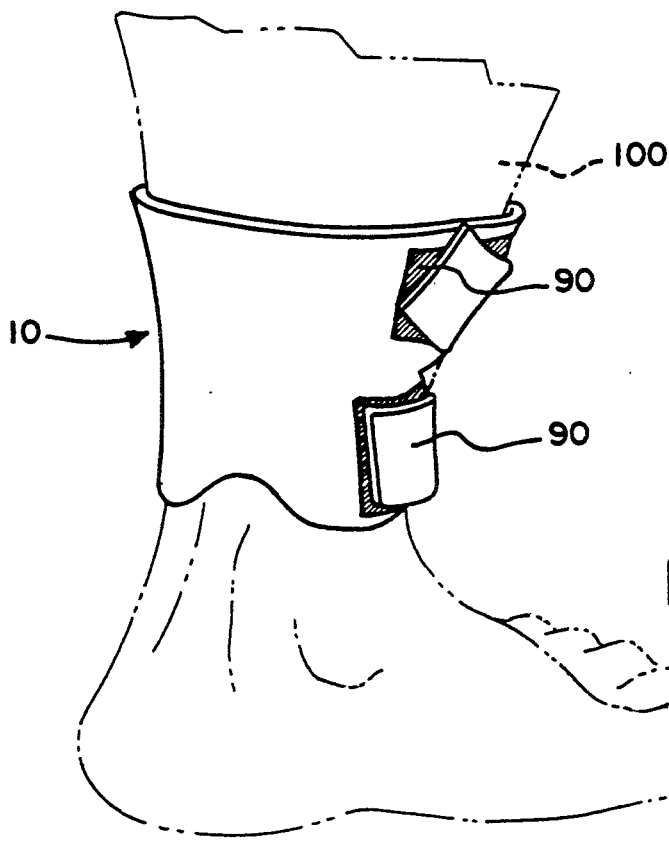
FIG. 5 is a three-quarter view of the present invention as applied to a patient's leg.
Figure 6:
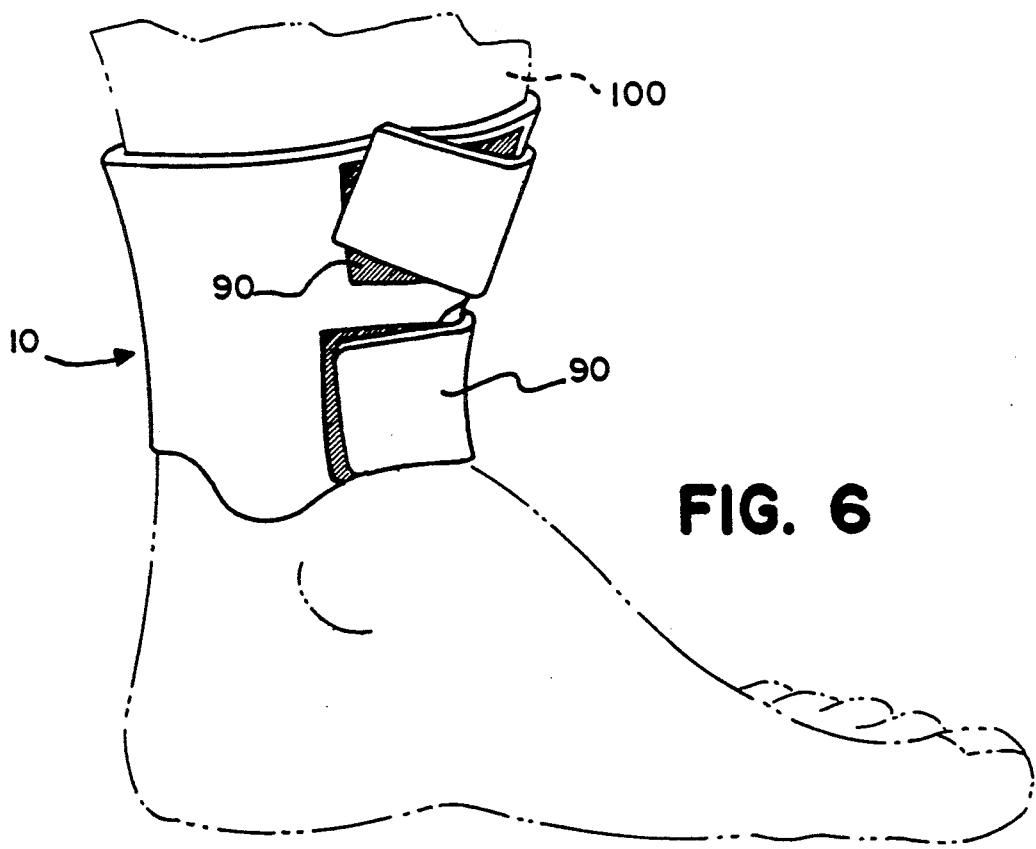
FIG. 6 is a side view of the strap as applied to a patient's leg.

The strap 30 is made from a material which allows flexibility of the lower leg which expands during exercise and activity, as well as accommodating any swelling that may have occurred due to the injury to the Achilles area. Neoprene is the preferred material, as it also permits optimal ability to tighten the device, assuring the proper anatomical fit and providing maximum counterforce to the Achilles tendon. The arms 35, 40 are approximately one and one-half inches (1½) wide. As illustrated in FIGS. 5 and 6, each of the corresponding arm pairs contains either hook or loop material 90 to provide tight and comfortable closure of the wrap 10 on various sizes of lower legs, allowing for universal fit. The use of hook and loop fasteners also permits easy application, adjustment, and removal of the wrap 10.

FIGS. 5 and 6 illustrate the wrap 10 as applied to a patient's leg 100. The wrap 10 is positioned on the lower leg with the base 45 of the pad 20 in the uppermost position. Since the most often involved area of the Achilles tendon, and therefore most vulnerable area, is known to be approximately two to three inches above the Achilles (calcaneal) tendon's attachment to the foot, it is important to position the wrap 10 so that the bump 60 lies immediately superior to that vulnerable section of the tendon. This placement will provide maximal counterforce and provide the greatest amount of relief of the tensile force normally transmitted to that part of the tendon through the Gastroc Soleus. The pad 20 should be applied to the leg in an equinus position to further maximize the compressive counterforce.

The superior arms 35 should be tightened first, establishing the optimal counterforce provided by the pad. The inferior arms 40 should be tightened next. Both are tightened and adjusted with the use of the hook and loop fasteners 90. The wrap should be snug, but should not interfere with the patient's circulation. No portion of the wrap should infringe on the talocrural or subtalar joints. Further, the wrap should not cross any portion of the ankle or foot. Once the proper application procedure has been demonstrated to the patient, the wrap 10 is designed for easy use and application without the need of assistance. The wrap 10 can therefore be applied or removed as the patient's activity level requires.

What is claimed is:

1. A wrap, having a topmost edge and a bottommost edge, said wrap including means for relieving inflammation of an Achilles tendon inferior comprising:

an adaptive compressive pad having a top surface for placement over said Achilles tendon, said pad having an area of depression on said top surface and a raised transverse bump in said area of depression for providing means for dispersing a force directed towards said Achilles tendon through said wrap and said pad further providing consistent support of said tendon throughout any activity;

an anatomically proportioned strapping system including means for applying and positioning said pad over said Achilles tendon and means for adapting to the contours of a patient's leg;

means for fastening said pad to said strapping system; and means for securing said pad to a patient so as to mount the wrap entirely above the patient's foot and ankle and avoid interfering with the range of motion of said patient's foot.

2. The wrap of claim 1 wherein said pad contains a multi-dimensional anterior surface, providing for multi-dimensional compression and support of said tendon.

3. The wrap of claim 2 wherein said pad is substantially triangular in shape, comprising a broad base and tapered sides.

4. The wrap of claim 3 wherein said anterior surface of said pad has a channel for accommodating said Achilles tendon.

5. The wrap of claim 4 wherein said means for dispersing a force directed towards said Achilles tendon comprises a raised transverse portion of said pad, said transverse portion being substantially perpendicular to said channel and substantially parallel to said base of said pad.

6. The wrap of claim 5 wherein said raised portion is positioned substantially along said base of said pad.

7. The wrap of claim 5 wherein said pad conforms to said Achilles tendon with continued use, providing multidimensional compression and supporting said tendon.

8. The wrap of claim 7 wherein said pad is mounted on said strapping system in an inverted manner, said base of said pad being positioned approximately adjacent to said top edge of said wrap.

9. The wrap of claim 8 wherein said strapping system possesses a top strap and a bottom strap.

10. The strapping system of claim 9 wherein said means for adapting to the contours of a patient's leg comprises said top strap angling upward from said top edge of said wrap and said bottom strap being positioned parallel to said top and bottom edges of said wrap and perpendicular to said channel in said pad.

11. The wrap of claim 10 wherein said securing means comprises a hook and loop fastener.

12. The wrap of claim 11 wherein means for fastening said pad to said strapping system comprises stitching means.

13. A wrap for relieving inflammation of an Achilles tendon inferior comprising:

an adaptive multidimensional compressive support pad having a top surface for placement over said Achilles tendon providing consistent support throughout movement;

a raised transverse bump in said pad providing a moment arm for dispersing a force transmitted through a Gastroc Soleus into said wrap, thereby relieving stress of contraction on said Achilles tendon;

an area of depression on said top surface said support pad inferior to said bump for receiving said tendon, thereby relieving said stress of contraction on said Achilles tendon and further dispersing said force transmitted through said Gastroc Soleus into said wrap;

means for applying and positioning said pad over said Achilles tendon so that said bump is positioned perpendicular to said Achilles tendon, said applying and positioning means comprising an anatomically proportioned strap designed to adapt to the contours of a patient's leg; and means for securing said wrap entirely above a patient's ankle so not to interfere with the range of movement of said patient's foot.

14. Method for relieving inflammation of a patient's Achilles tendon inferior, said Achilles tendon being attached to a patient's foot and being part of a Gastroc Soleus Complex, said method comprising:

placing an Achilles tendon support wrap over a patient's Achilles tendon, said wrap comprising: a multidimensional compressive support pad having a top surface, said pad containing a transverse raised portion and a cut-out channel perpendicular to and inferior to said raised portion on said top surface, means to apply and align said pad, and means to secure said pad;

relieving the stresses of contraction on said Achilles tendon by positioning said raised portion of said support pad above a point of attachment of said Achilles tendon to the foot, aligning said channel with said patient's Achilles tendon so as to receive said tendon and thereby providing continued support for said tendon during activity;

dispersing forces from the Gastroc Soleus Complex through the raised portion and the wrap; and using an anatomically proportioned strap, said strap being designed for adapting to contours of a patient's leg, to prevent slippage of said pad and to secure said pad to said patient without infringing on movement and range of action of the patient's foot and ankle, thereby providing consistent support along said tendon throughout an activity.

* * * * *